US00PP23833P2

(12) United States Plant Patent
Danziger

(10) Patent No.: US PP23,833 P2
(45) Date of Patent: Aug. 13, 2013

(54) ***GAILLARDIA* PLANT NAMED 'DGAL902'**

(50) Latin Name: *Gaillardia pulchella*
Varietal Denomination: DGAL902

(75) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 1 day.

(21) Appl. No.: 13/317,215

(22) Filed: Oct. 12, 2011

(51) Int. Cl.
*A01H 5/00* (2006.01)

(52) U.S. Cl.
USPC ..... Plt./431

(58) Field of Classification Search
USPC ..... Plt./431
See application file for complete search history.

*Primary Examiner* — Susan McCormick Ewoldt
(74) *Attorney, Agent, or Firm* — Cassandra Bright

(57) ABSTRACT

A new and distinct *Gaillardia* cultivar named 'DGAL902' is disclosed, characterized by a distinctive lemon yellow flower, somewhat compact plant habit, good branching and abundant flowering. The new variety begins blooming early in the season and flowers over a long period of time. The new variety is a *Gaillardia*, normally produced as an outdoor garden or container plant.

2 Drawing Sheets

Figure 1:
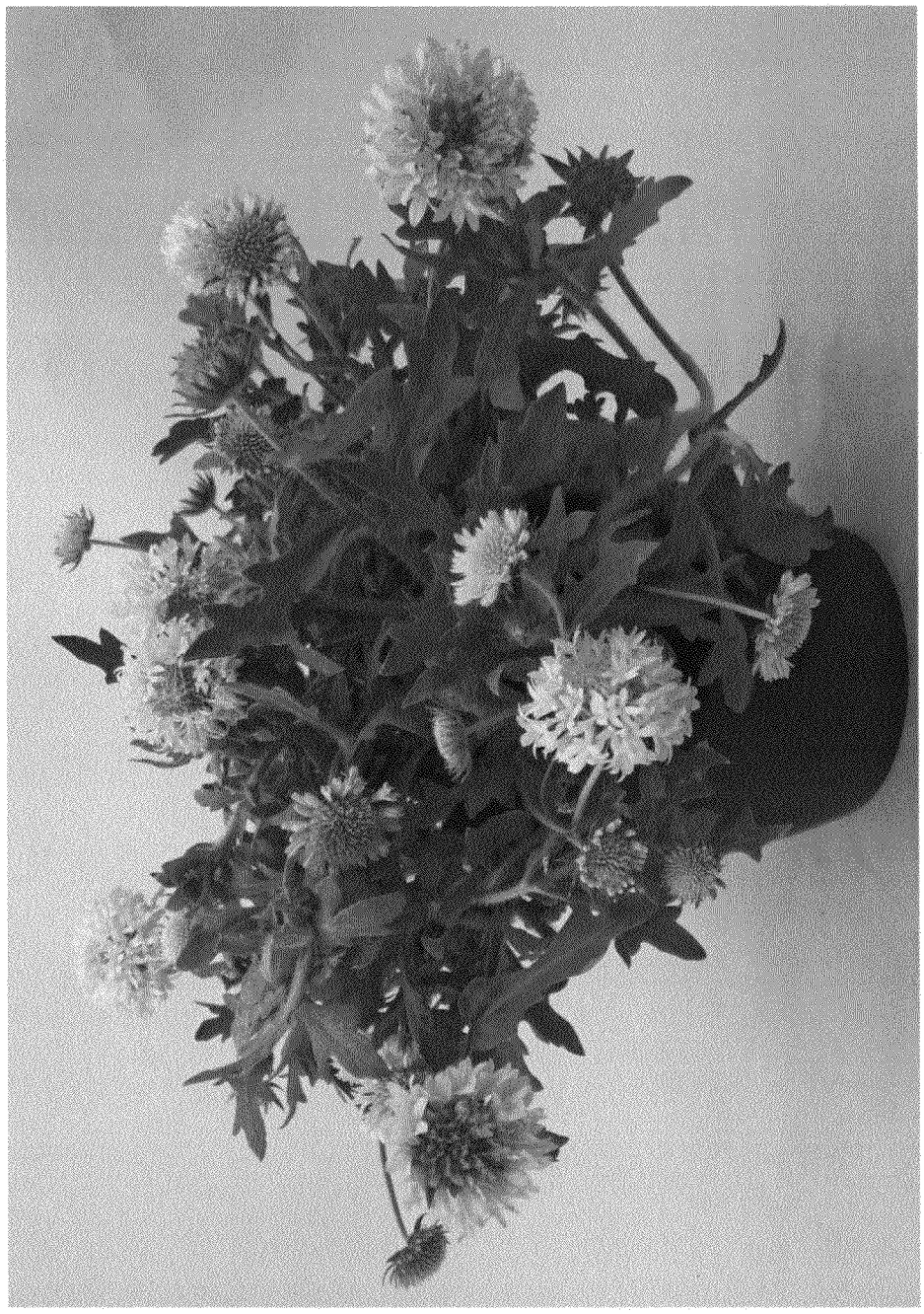

Latin name of the genus and species: *Gaillardia pulchella.*
Variety denomination: 'DGAL902'.

BACKGROUND OF THE INVENTION

The new *Gaillardia* cultivar is a product of a planned breeding program conducted by the inventor, Gavriel Danziger, in Moshav Mishmar Hashiva, Israel. The objective of the breeding program was to produce new *Gaillardia* varieties for ornamental commercial applications. The cross resulting in this new variety was made during August 2005.

The seed parent is the unpatented, proprietary seedling variety referred to as *Gaillardia pulchella* 'GAI-31'. The pollen parent is unknown, as the crossing resulting in 'DGAL902' was an open pollination, with unidentifiable pollen parents. The new variety was discovered in July 2006 by the inventor in a group of seedlings resulting from the 2005 crossing, in a research greenhouse in Moshav Mishmar Hashiva, Israel.

Asexual reproduction of the new cultivar 'DGAL902' by vegetative cuttings was first performed at a research greenhouse in Moshav Mishmar Hashiva, Israel in February 2007 and has shown that the unique features of this cultivar are stable and reproduced true to type in successive generations.

SUMMARY OF THE INVENTION

The cultivar 'DGAL902' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DGAL902' These characteristics in combination distinguish 'DGAL902' as a new and distinct *Gaillardia* cultivar:

1. Somewhat compact habit
2. Highly floriferous
3. Long flowering season
4. Good branching 5. Early blooming
6. Unique lemon yellow flower color Plants of the new cultivar 'DGAL902' are similar to plants of the seed parent, *Gaillardia pulchella* 'GAI-31' in most horticultural characteristics, however, plants of the new cultivar 'DGAL902' produce more flowers and branches on a more compact plant than 'GAI-31'.

COMMERCIAL COMPARISON

Plants of the new cultivar 'DGAL902' are comparable to the variety *Gaillardia pulchella* 'Torch Red Embers', patent status unknown after reasonable search by the applicant. The two *Gaillardia* varieties are similar in most horticultural characteristics, however, the new variety 'DGAL902' differs in having more flowers per plant, different colored flowers and a more compact, and spreading plant habit. Additionally, 'DGAL902' has semi-double flowers, compared to the double flowers of 'Torch Red Embers'.

Plants of the new cultivar 'DGAL902' can also be compared to the commercial variety *Gaillardia* 'BALTORYELL' U.S. Plant Pat. No. 15,966. These varieties are similar in most horticultural characteristics, however plants of 'DGAL902' produce lighter yellow flowers than 'BALTORYELL'. 'DGAL902' produces semi double flowers, whereas 'BALTORYELL' produces fully double flowers. Additionally, 'DGAL902' has more flowers per plant, and a more compact, spreading plant habit.

BRIEF DESCRIPTION OF THE PHOTOGRAPHS

The accompanying photograph in FIG. 1 illustrates in full color a typical plant of 'DGAL902' grown in a greenhouse, in a 12 cm pot.

Figure 2:
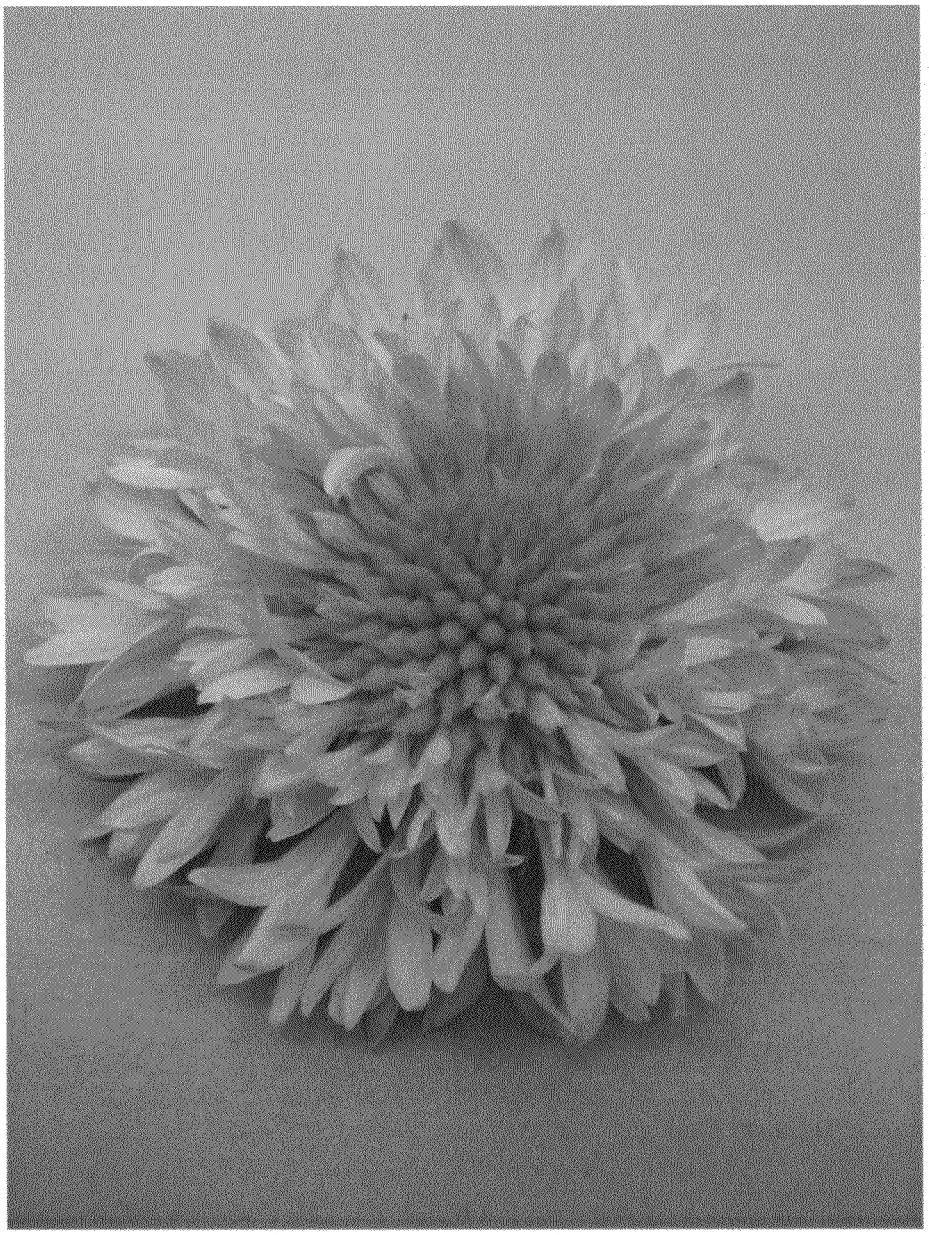

FIG. 2 illustrates in full color a close up of a single flower of 'DGAL902'.

Age of the plant photographed is approximately 8 weeks from a rooted cutting. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'DGAL902' plants grown outdoors during Spring in Moshav Mishmar Hashiva, Israel. The growing temperature ranged from 18° C. to 28° C. during the day and from 13° C. to 18° C. during the night. General light conditions are bright, normal sunlight. Measurements and numerical values represent averages of typical plant types. Plants are approximately 12 weeks old from a rooted cutting.

Botanical classification: *Gaillardia pulchella* 'DGAL902'.

PROPAGATION

Time to initiate roots: About 3 to 5 days at approximately 20° C.

Root description: Fleshy, well branched. Colored near RHS Green-White 157C.

PLANT

Age of plant described: Approximately 84 days from a rooted cutting.

Growth habit: Compact and slightly spreading.

Pot size of plant described: 12 cm.

Height: 25 cm.

Plant spread: 45 cm.

Growth rate: Moderate.

Branching characteristics: Well branched, basal branching.

Length of primary lateral branches: Approximately 10 cm.

Quantity of primary lateral branches: Approximately 20.

Characteristics of primary lateral branches:

- *Diameter.*—0.3 cm.
- *Color.*—Near RHS Yellow-Green 144B.
- *Texture.*—Densely covered with short bristly hairs.
- *Strength.*—Very strong.

Internodes length: 1.5-2.0 cm.

FOLIAGE

Leaf:

- *Shape.*—Pinnatisect.
- *Quantity.*—Approximately 5-8 per branch.
- *Average length.*—5-7 cm.
- *Average width.*—1.5-3 cm.
- *Apex.*—Acute.
- *Base.*—Cordate.
- *Margin.*—Entire.
- *Texture of top surface.*—Somewhat rough.
- *Texture of bottom surface.*—Somewhat rough.
- *Pubescence.*—Delicately pubescent.
- *Angle of attachment.*—45 degrees upwards.
- *Color.*—Young foliage upper side: Near RHS Green 137C. Young foliage under side: Near RHS Green 137B. Mature foliage upper side: Near RHS Green 137A. Mature foliage under side: Near RHS Green 138B.
- *Venation.*—Type: Pinnate. Venation color upper side: Near RHS Green 138D. Venation color under side: Near RHS Green 138C.
- *Petiole.*—Sessile.

FLOWER

Natural flowering season: March to August, long day conditions.

Time to flowering from rooted cutting: 4 to 6 weeks.

Inflorescence and flower type and habit: Solitary, semi-double.

Rate of flower opening: 3 to 5 days from bud to fully opened flower.

Flower longevity on plant: 5 to 7 days.

Persistent or self-cleaning: Self-cleaning.

Flower size:

- *Diameter of entire flower.*—Approximately 5.5 cm.
- *Depth of flower.*—Approximately 2 cm.
- *Disc diameter.*—Approximately cm. 2.5 cm.
- *Receptacle shape.*—No receptacle.
- *Quantity of inflorescences per lateral stem.*—3-5.
- *Quantity of open inflorescences and buds per plant.*—15-20.

Bud:

- *Shape.*—Flattened globular.
- *Length.*—0.5-1.0 cm.
- *Diameter.*—1.4-1.8 cm.
- *Color.*—Near RHS Yellow-Green 144B.

Ray florets:

- *Quantity.*—120.
- *Arrangement.*—Rotate in a triple whorl.
- *Length.*—2-2.5 cm.
- *Width.*—1.5-1.8 cm.
- *Shape.*—Trumpet-Shaped.
- *Apex.*—Fused, appears to be 5 separate apexes, however, fused to one.
- *Base.*—Fused into tubular shape.
- *Margin.*—Entire.
- *Texture, upper and lower surfaces.*—Smooth, slightly ribbed longwise.

Color:

- *When opening, external surface.*—Near RHS Yellow 6D near center and Yellow 6C at the tips.
- *When opening, internal surface.*—Near RHS Yellow 2D, near center and Yellow 10B at the tips.
- *Fully opened, external surface.*—Near RHS Green-Yellow 1C near center and Yellow 11C at the tips.
- *Fully opened, internal surface.*—Near RHS Yellow 1D near center Yellow 12C at the tips.

Disc florets: Disc flowers are only rudimentary flowers. Insiginifcant, with reproductive organs present.

- *Quantity.*—120.
- *Arrangement.*—Spirally placed on disc.
- *Length.*—0.8 cm.
- *Diameter.*—0.3 cm.
- *Shape.*—Elliptic.
- *Apex.*—Acute.
- *Base.*—Fused.
- *Margin.*—Entire.
- *Texture, upper and lower surfaces.*—Densely covered with short bristly hairs.

Color: Near RHS White 155A near center and Greyed-Purple group 187A at the tips.

Phyllaries/involucal bracts:
*Quantity*.—Approximately 60.
*Length*.—1 cm.
*Width*.—0.2-0.4 cm.
*Shape*.—Lanceolate to ovate.
*Apex*.—Acute.
*Base*.—Wedge shaped.
*Texture*.—Dull, covered with short hairs.
*Margin*.—Entire, with short hairs directly on margin.
*Color*.—Near RHS Green 138A.
Peduncles:
*Length*.—Average 6-8 cm.
*Diameter*.—0.2 cm.
*Angle*.—About 45° to the lateral branch.
*Strength*.—Moderate.
*Texture*.—Slightly glossy.
*Color*.—Near RHS Yellow-Green 147D.
Fragrance: Slightly sweet scent.

REPRODUCTIVE ORGANS

Disc florets:
Stamens:
*Number*.—6.
Anthers:
*Shape*.—Ligulate.
*Length*.—Approximately 0.5 mm.
*Color*.—Near RHS Yellow 2D.
*Pollen*.—Color: Near RHS Yellow 13A. Quantity: Moderate amount.
Pistil:
*Number*.—One present.
*Length*.—10 mm.
*Style*.—Tubular.
*Length*.—4 mm.
*Color*.—Near Yellow 6D.
*Stigma*.—Shape: Bifid. Color: Near Yellow 6D. Ovary Color: Near White 155A.
Ray florets: No reproductive organs present.

OTHER CHARACTERISTICS

Seeds and fruits: 50-70 seeds per flower, Shape: oblong triangle, size: 0.2 cm long by 0.15 cm wide, with spiny crown on top 0.3 cm long by 0.2 wide.
Disease/pest resistance: Neither resistance nor susceptibility to pathogens and pests common to *Gaillardia* have been observed.
Temperature tolerance: The new variety exhibits a good temperature tolerance range for *Gaillardia*. Known tolerance for high temperatures to at least 35° C. Low temperature tolerance unknown.
What is claimed is:
1. A new and distinct cultivar of *Gaillardia* plant named 'DGAL902' as herein illustrated and described.

* * * * *